(12) United States Patent
Sabatini et al.

(10) Patent No.: US 9,994,532 B1
(45) Date of Patent: Jun. 12, 2018

(54) BIS-ISOXAZOLE TETRANITRATE (BITN): A HIGH-ENERGY PROPELLANT PLASTICIZER AND MELT-CASTABLE EUTECTIC EXPLOSIVE INGREDIENT

(71) Applicant: THE UNITED STATES OF AMERICA AS REPRESENTED BY THE SECRETARY OF THE ARMY—U.S. ARMY RESEARCH LABORATORY, Washington, DC (US)

(72) Inventors: Jesse J. Sabatini, Bel Air, MD (US); Gregory W Drake, Madison, AL (US); Leah A. Wingard, Landenberg, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days. days.

(21) Appl. No.: 15/686,521

(22) Filed: Aug. 25, 2017

(51) Int. Cl.
*C07D 261/08* (2006.01)
*C06B 25/00* (2006.01)

(52) U.S. Cl.
CPC ............ *C07D 261/08* (2013.01); *C06B 25/00* (2013.01)

(58) Field of Classification Search
None
See application file for complete search history.

(56) References Cited

U.S. PATENT DOCUMENTS 9,296,664 B2    3/2016 Klapotke et al.
2007/0197801 A1 8/2007 Bolk et al.

OTHER PUBLICATIONS

Wingard, et al., Eur. J. Org. Chem., 13:1765 (published online Apr. 5, 2017). (Year: 2017).*

* cited by examiner

*Primary Examiner* — Michael Barker
(74) *Attorney, Agent, or Firm* — Robert Thompson (57) ABSTRACT

A method and compound includes mixing a salt compound to 2-butyne-1,4-diol in an alcohol to create a mixture; adding a solution of dichloroglyoxime in an alcohol to the mixture to create 3,3'-bis-isoxazole-4,4',5,5'-tetryltetramethanol; and nitrating the 3,3'-bis-isoxazole-4,4',5,5'-tetryltetramethanol to create 3,3'-bis-isoxazole-4,4',5,5'-tetrylbis(methylene) tetranitrate, which has the structural formula:

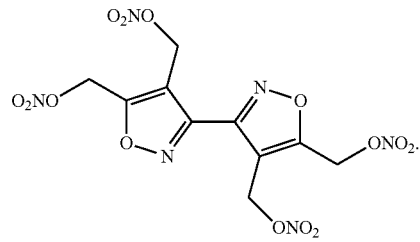

The alcohol may include ethanol, wherein the adding may occur at 60° C., or alternatively the adding may occur at 80° C. The alcohol may include n-butanol, wherein the adding may occur at 100° C., or alternatively the adding may occur at 120° C. The mixing may occur at 120° C. The method may further include cooling the nitrated 3,3'-bis-isoxazole-4,4',5,5'-tetryltetramethanol to 0° C.; stirring the cooled nitrated 3,3'-bis-isoxazole-4,4',5,5'-tetryltetramethanol for at least four hours creating a precipitate; warming the precipitate; pouring the precipitate onto ice while stirring creating a solid material; collecting the solid material; and drying the solid material to yield the 3,3'-bis-isoxazole-4,4',5,5'-tetrylbis(methylene) tetranitrate.

14 Claims, 11 Drawing Sheets

BIS-ISOXAZOLE TETRANITRATE (BITN): A HIGH-ENERGY PROPELLANT PLASTICIZER AND MELT-CASTABLE EUTECTIC EXPLOSIVE INGREDIENT

GOVERNMENT INTEREST

The embodiments herein may be manufactured, used, and/or licensed by or for the United States Government without the payment of royalties thereon.

BACKGROUND

Technical Field

The embodiments herein generally relate to energetic materials, and more particularly to energetic materials used in explosives and propellants.

Description of the Related Art

The development of high-energy density materials (HEDMs) with good performance and low sensitivity is a common goal amongst those with an interest in the field of energetic materials. HEDMs are divided into two main groups: explosives and propellants. Explosive materials contain a significant amount of potential energy that produces a significant amount of light, heat, sound and pressure when this energy is released suddenly. When this phenomenon occurs, it is known as an explosion. A propellant is an energetic substance that is used to project a vehicle, bullet or other object, typically through the formation of hot, low molecular weight gases.

Two respective sub-areas of explosives and propellants are melt-castable materials and energetic plasticizers. It is known in the industry that an ideal melt-cast material is defined as having a low vapor pressure (inhalation toxicity), a melting point between 70-120° C., a significant difference between the melting temperature and the temperature of decomposition, a high density, low sensitivity, and a "greener" synthesis. Traditional melt-cast technologies are TNT-based, but environmental concerns have led to its replacement with dinitroanisole (DNAN)-based melt-castable eutectic formulations, as known in the industry. However, DNAN, with a density of 1.52 gcm$^{-3}$, and a detonation velocity of 5670 ms$^{-1}$, is a less powerful explosive than TNT according to conventional thought. There is a need to develop TNT replacements for melt-castable explosive applications. Thus, there is an interest in developing new melt-castable candidates that can be formulated to probe their potential applications.

As the name implies, a plasticizer, when added to a formulation, enhances the fluidity or plasticity of the material. Energetic plasticizers are used to improve the physical properties, to double as a fuel, and to improve the overall energy yield of a formulation. Currently, most fielded nitrate-based plasticizers are high-energy molecules, which to the formulator, are as oxygen balanced as possible to obtain the highest performance of their respective propellant (gun and rocket). One of the most popular nitrate ester-based plasticizers is the oily liquid nitroglycerin (NG). Moreover, a very useful and applicable gel is formed when NG is mixed with nitrocellulose (NC). This gel has been used for many years to produce blasting gelatin, gelatin dynamite, and ballistite, the first double-base propellant smokeless powder. NC and NG make up an optimal energetic composition. The former helps impart mechanical strength to the propellant, while the latter assists in increasing the energy and burning rate of the propellant.

Unfortunately, oxygen balanced nitrate-based plasticizers such as NG tend to be quite sensitive to a variety of thermal and mechanical insults. Typically, most liquid nitrates have rather high volatility in regards to their molecular weight. Coupled with weak carbon-nitroxy linkages, it has been shown that this often results in premature volatilization/decomposition into reactive gaseous products under extended heating/and or long-term aging, resulting in detonable materials. Unfortunately, NG, which is widely regarded as the work horse energetic plasticizer, suffers from a high degree of thermal instability, as it decomposes at 50° C. NG also tends to require chemical stabilization, as it is too reactive to be used in practical applications as a standalone ingredient. Hence, energetic plasticizers such as NG suffer from high volatility in cook-off scenarios, leading to gas phase species which are highly detonable. There are numerous nitrate esters that are known, but many of these materials contain secondary nitrate ester functionalities, which are inherently unstable. It is further known that nitrate functionalities tend to suffer from stability issues (i.e., nitroglycerin (NG)). However, this is mainly because such nitrate functionalities are present on secondary carbons. Furthermore, many nitrates decompose at temperatures around 150° C. Such melt-castable candidates should possess as much power as possible. There is a need for high-energy plasticizers in propellants that have the potential to replace the inert plasticizers, such as phthalate-, adipate-, and triacetin-based plasticizers. Accordingly, there is a need to develop new energetic materials that overcome the aforementioned safety and performance concerns.

SUMMARY

In view of the foregoing, an embodiment herein provides a method comprising mixing a salt compound to 2-butyne-1,4-diol in an alcohol to create a mixture; adding a solution of dichloroglyoxime in an alcohol to the mixture to create 3,3'-bis-isoxazole-4,4',5,5'-tetryltetramethanol; and nitrating the 3,3'-bis-isoxazole-4,4',5,5'-tetryltetramethanol to create 3,3'-bis-isoxazole-4,4',5,5'-tetrylbis(methylene) tetranitrate. The 3,3'-bis-isoxazole-4,4',5,5'-tetrylbis(methylene) tetranitrate comprises the structural formula:

The alcohol may comprise ethanol, wherein the adding may occur at 60° C., or alternatively the adding may occur at 80° C. The alcohol may comprise n-butanol, wherein the adding may occur at 100° C., or alternatively the adding may occur at 120° C. The mixing may occur at 120° C. The method may further comprise nitrating the 3,3'-bis-isoxazole-4,4',5,5'-tetryltetramethanol with nitric acid. The nitric acid may comprise at least a concentration of 90% nitric acid in water. The method may further comprise nitrating the 3,3'-biisoxazole-4,4',5,5'-tetryltetramethanol with 100% nitric acid and acetic anhydride. The adding may occur over at least a four-hour period. The method may further comprise cooling the nitrated 3,3'-bis-isoxazole-4,4',5,5'-tetryltetramethanol to 0° C.; stirring the cooled nitrated 3,3'-bis-isoxazole-4,4',5,5'-tetryltetramethanol for at least four hours creating a precipitate; warming the precipitate; pouring the precipitate onto ice while stirring creating a solid material; collecting the solid material; and drying the solid material to yield the 3,3'-bis-isoxazole-4,4',5,5'-tetrylbis(methylene) tetranitrate.

Another embodiment provides a compound having the structural formula:

The compound may be formed by mixing a salt compound to 2-butyne-1,4-diol in alcohol to create a mixture; adding a solution of dichloroglyoxime in alcohol to the mixture to create 3,3'-bis-isoxazole-4,4',5,5'-tetryltetramethanol; and nitrating the 3,3'-bis-isoxazole-4,4',5,5'-tetryltetramethanol to create 3,3'-bis-isoxazole-4,4',5,5'-tetrylbis(methylene) tetranitrate. The alcohol may comprise any of ethanol and n-butanol. The mixing may occur at 120° C. The nitration may occur with nitric acid. The compound may be further formed by cooling the nitrated 3,3'-bis-isoxazole-4,4',5,5'-tetryltetramethanol to 0° C.; stirring the cooled nitrated 3,3'-bis-isoxazole-4,4',5,5'-tetryltetramethanol for at least four hours creating a precipitate; warming the precipitate; pouring the precipitate onto ice while stirring creating a solid material; collecting the solid material; and drying the solid material to yield the 3,3'-bis-isoxazole-4,4',5,5'-tetrylbis(methylene) tetranitrate.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide for the synthesis, energetic properties, and analytical properties of a new energetic molecule, 3,3'-bis-isoxazole-4,4',5,5'-tetrylbis(methylene) tetranitrate (BITN). Referring now to the drawings, and more particularly to FIGS. 1 through 11, where similar reference characters denote corresponding features consistently throughout the figures, there are shown preferred embodiments.

The embodiments herein provide for a new molecule, BITN, which can serve energetic functions as an energetic plasticizer in rocket and gun propellant formulations, as well as a melt-castable eutectic explosive ingredient. Because BITN possesses some weak Lewis basic functionality (i.e., N—O isoxazole linkage), this material will favorably interact with nitrocellulose (NC) in double-base propellant formulations. Thus, BITN can provide benefits when interacting with NC in terms of being a good wetting agent and surfactant.

Figure 1:
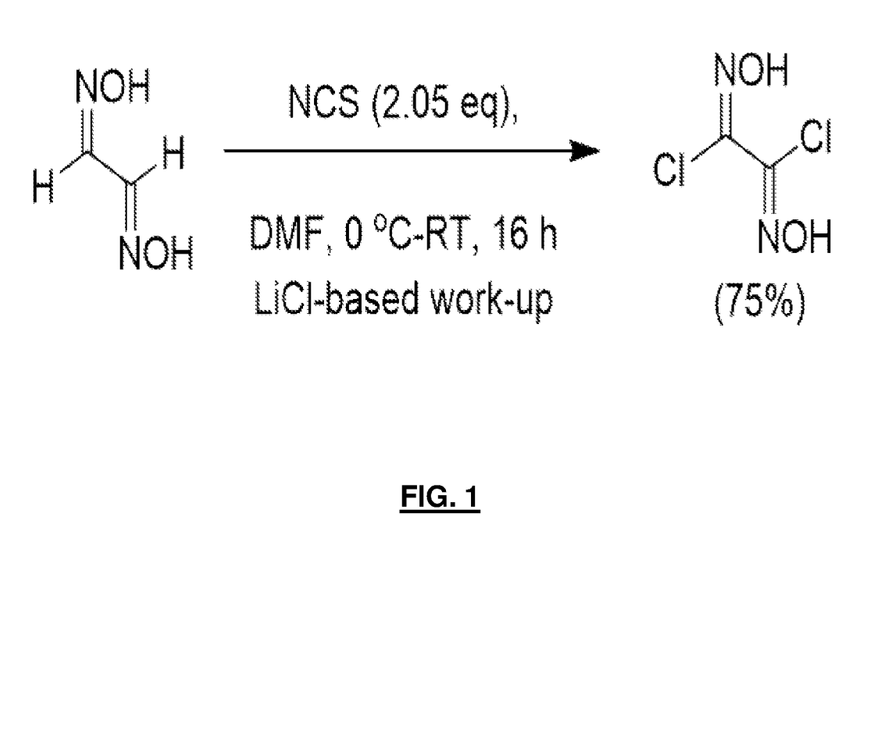
FIG. 1 illustrates a chemical diagram of the synthesis of dichloroglyoxime according to an embodiment herein.
Figure 2:
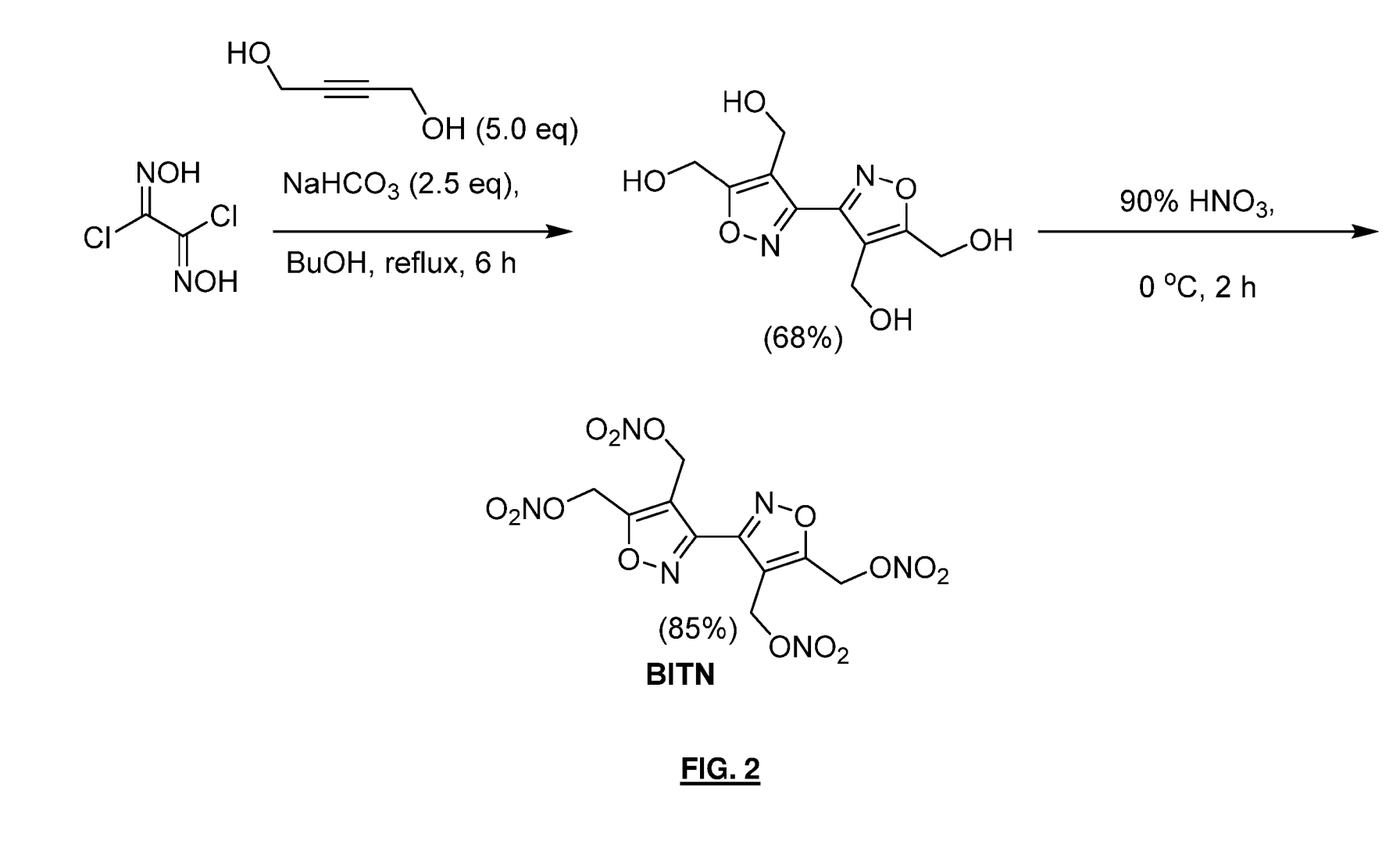
FIG. 2 illustrates a chemical diagram of the synthesis of 3,3'-bis-isoxazole-4,4',5,5'-tetrylbis(methylene) tetranitrate (BITN) according to an embodiment herein.
Figure 3:
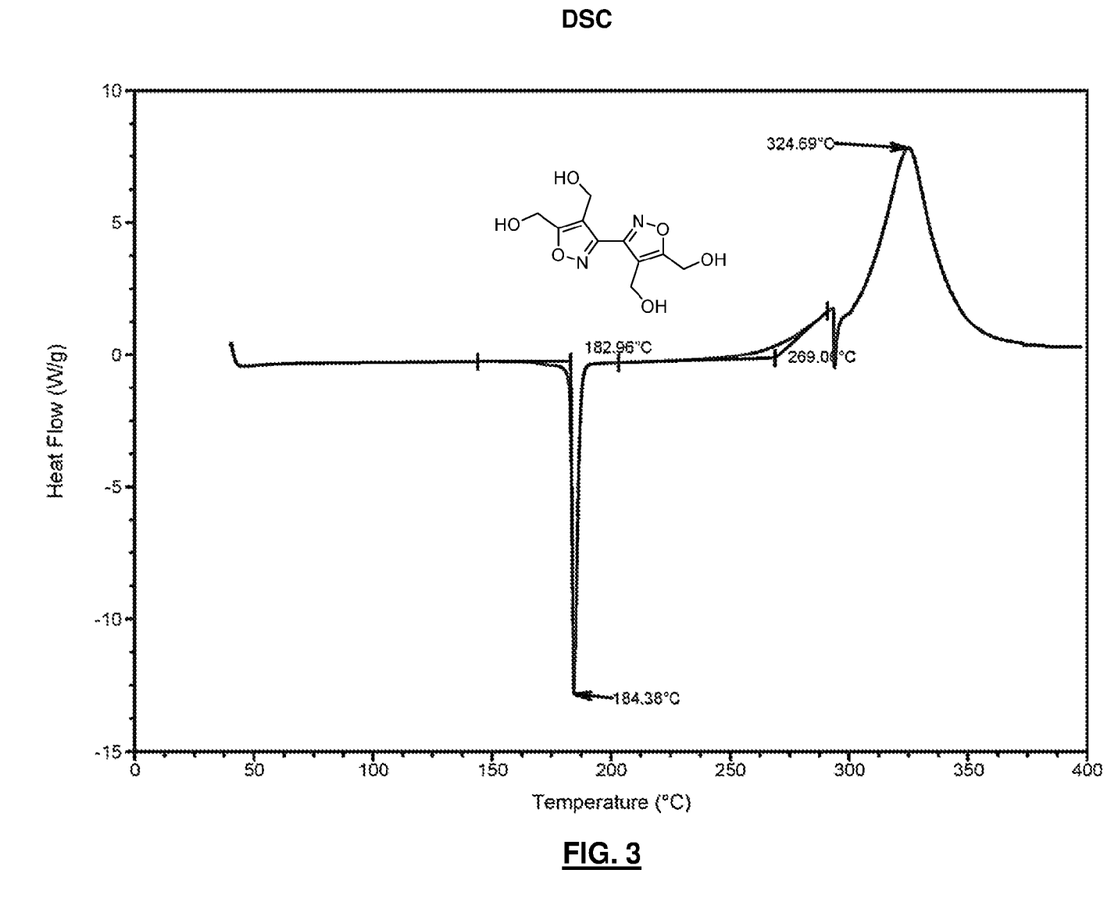
FIG. 3 is a graphical illustration of differential scanning calorimetry (DSC) curves of 3,3'-bis-isoxazole-4,4',5,5'-tetryltetramethanol according to an embodiment herein.
Figure 4:
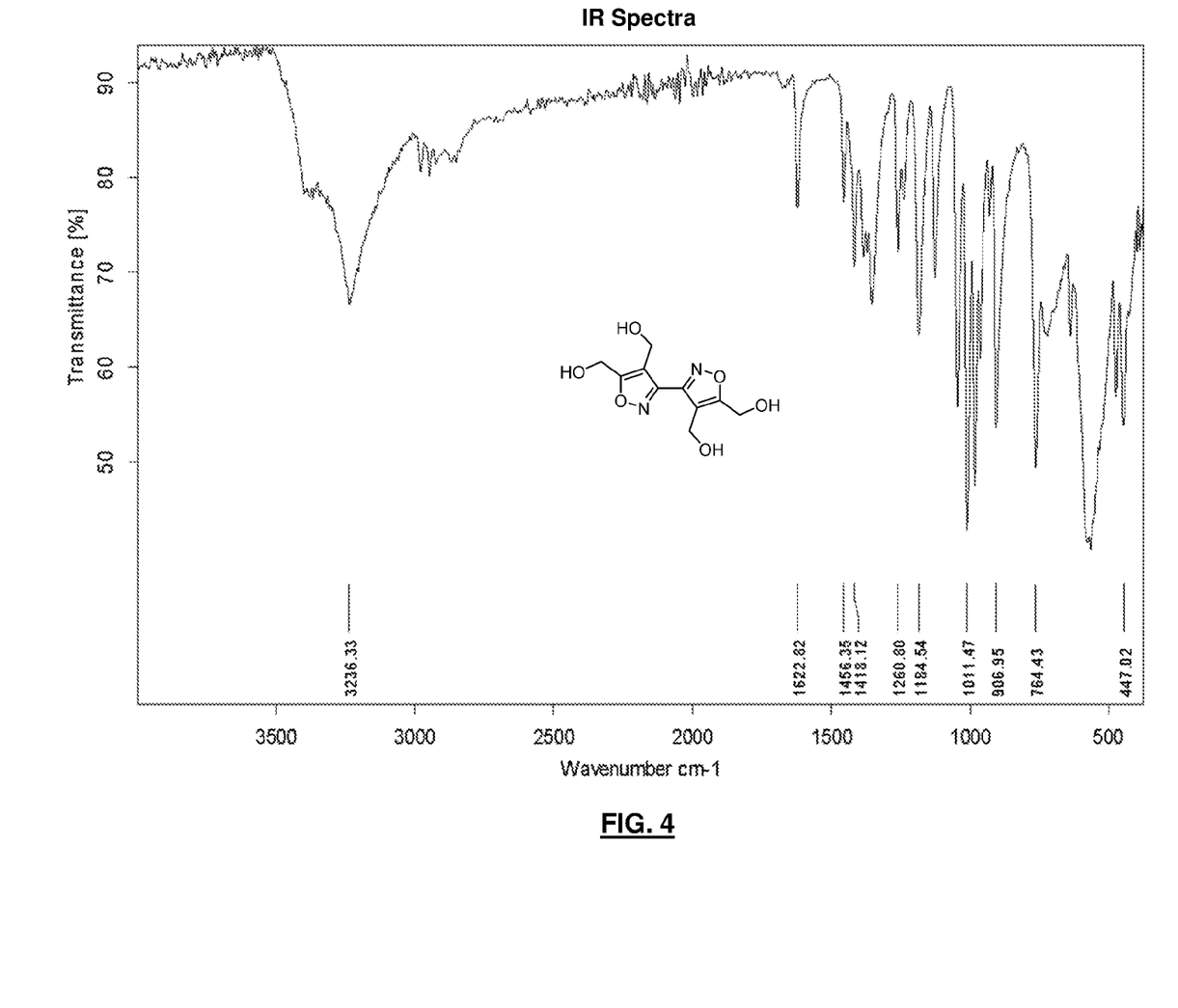
FIG. 4 is a graphical illustration of an infrared (IR) spectra of 3,3'-bis-isoxazole-4,4',5,5'-tetryltetramethanol according to an embodiment herein.
Figure 5:
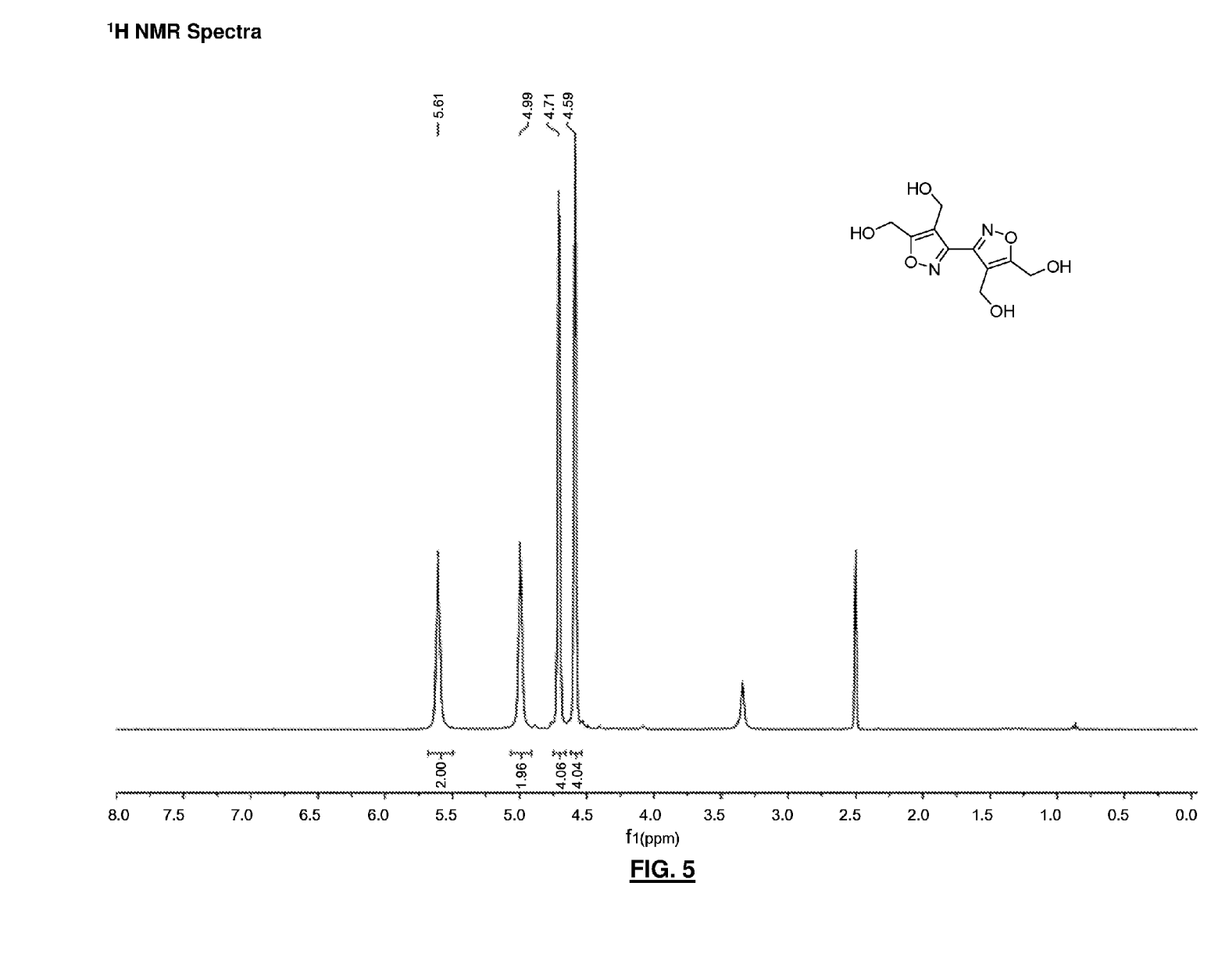
FIG. 5 is a graphical illustration of an $^1$H nuclear magnetic resonance (NMR) spectra of 3,3'-bis-isoxazole-4,4',5,5'-tetryltetramethanol according to an embodiment herein.
Figure 6:
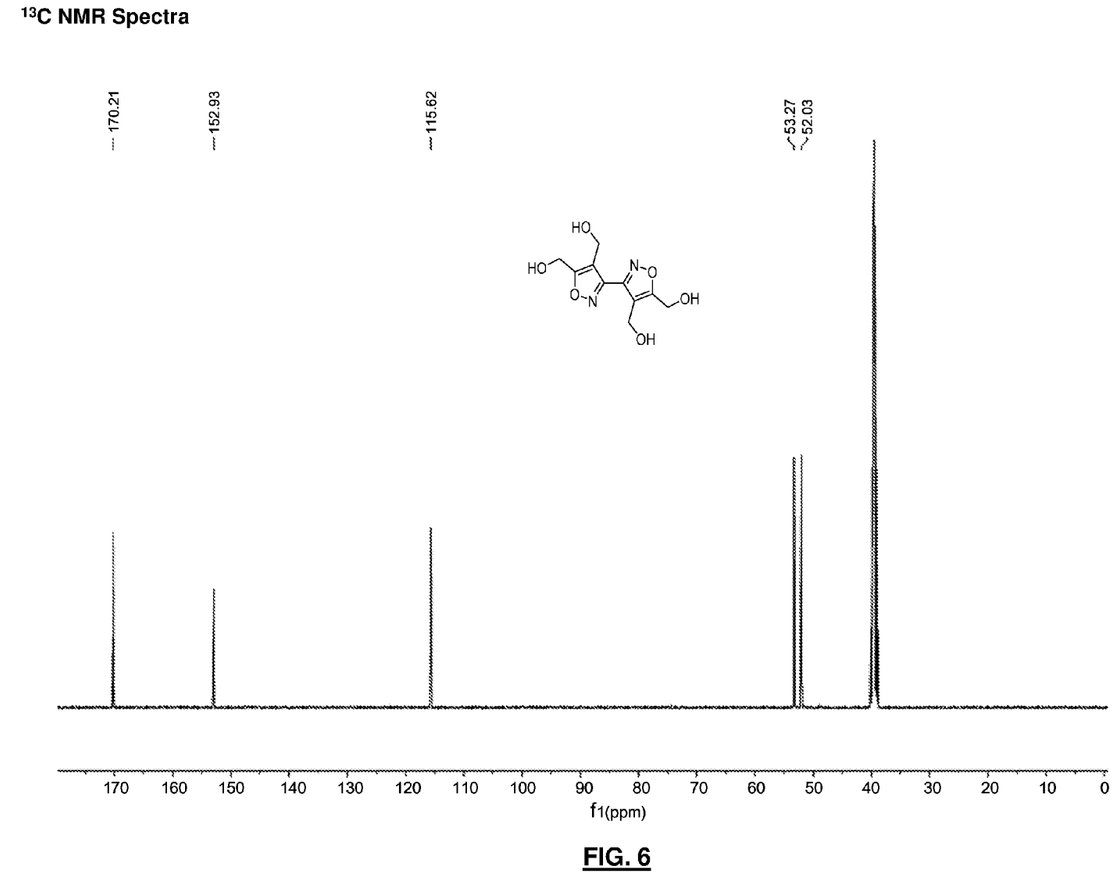
FIG. 6 is a graphical illustration of an $^{13}$C NMR spectra of 3,3'-bis-isoxazole-4,4',5,5'-tetryltetramethanol according to an embodiment herein.
Figure 7:
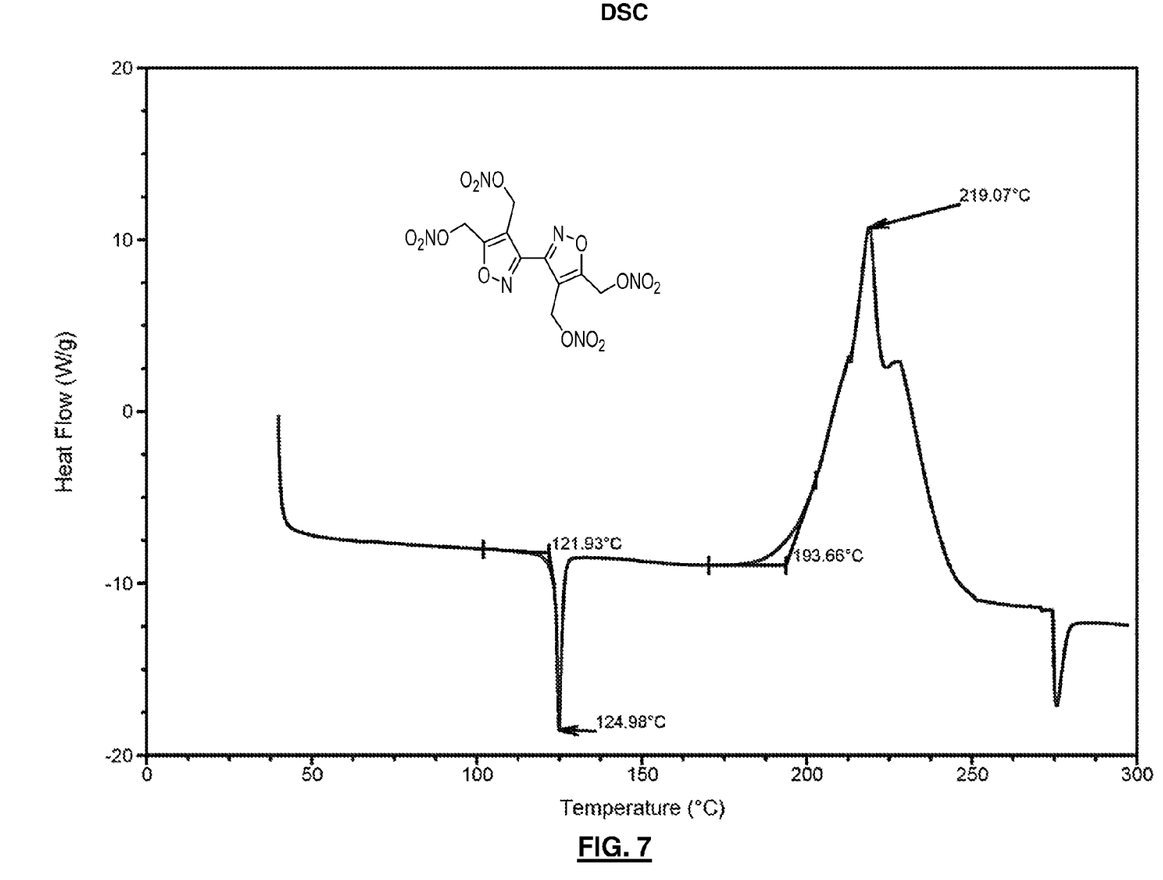
FIG. 7 is a graphical illustration of DSC curves of 3,3'-bis-isoxazole-4,4',5,5'-tetrylbis(methylene) tetranitrate (BITN) according to an embodiment herein.
Figure 8:
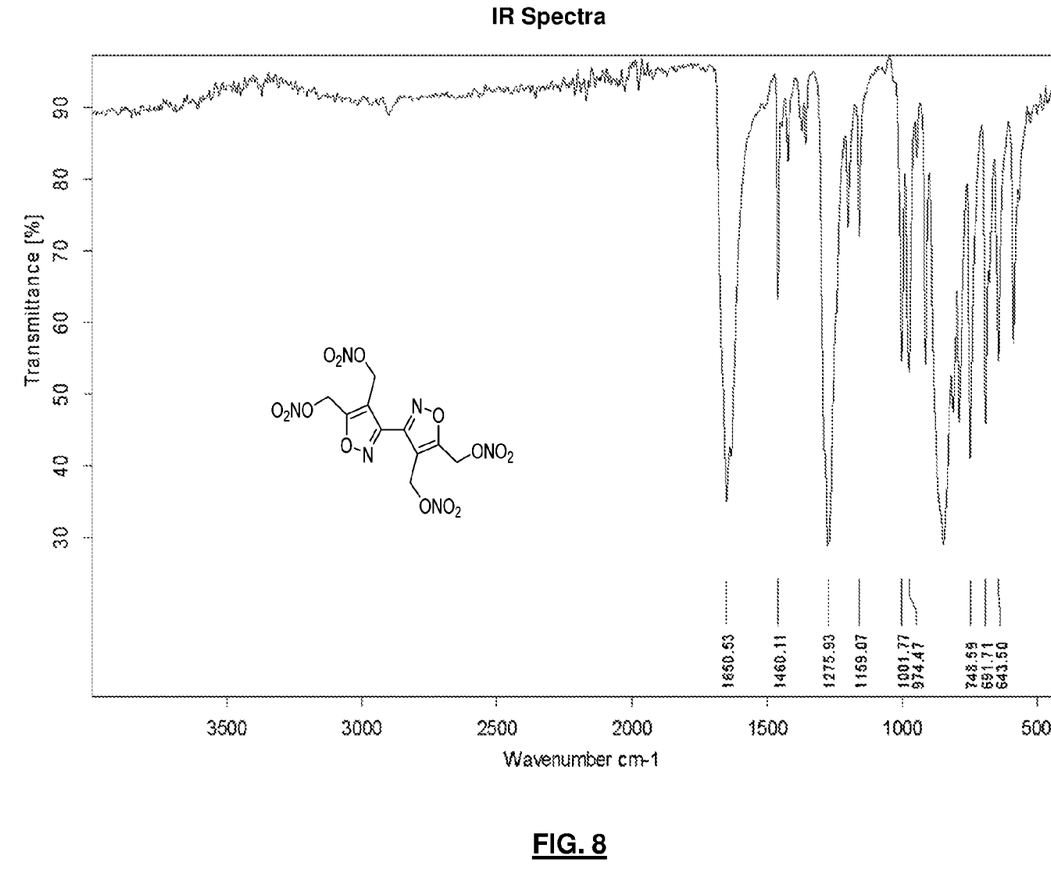
FIG. 8 is a graphical illustration of an IR spectra of 3,3'-bis-isoxazole-4,4',5,5'-tetrylbis(methylene) tetranitrate (BITN) according to an embodiment herein.
Figure 9:
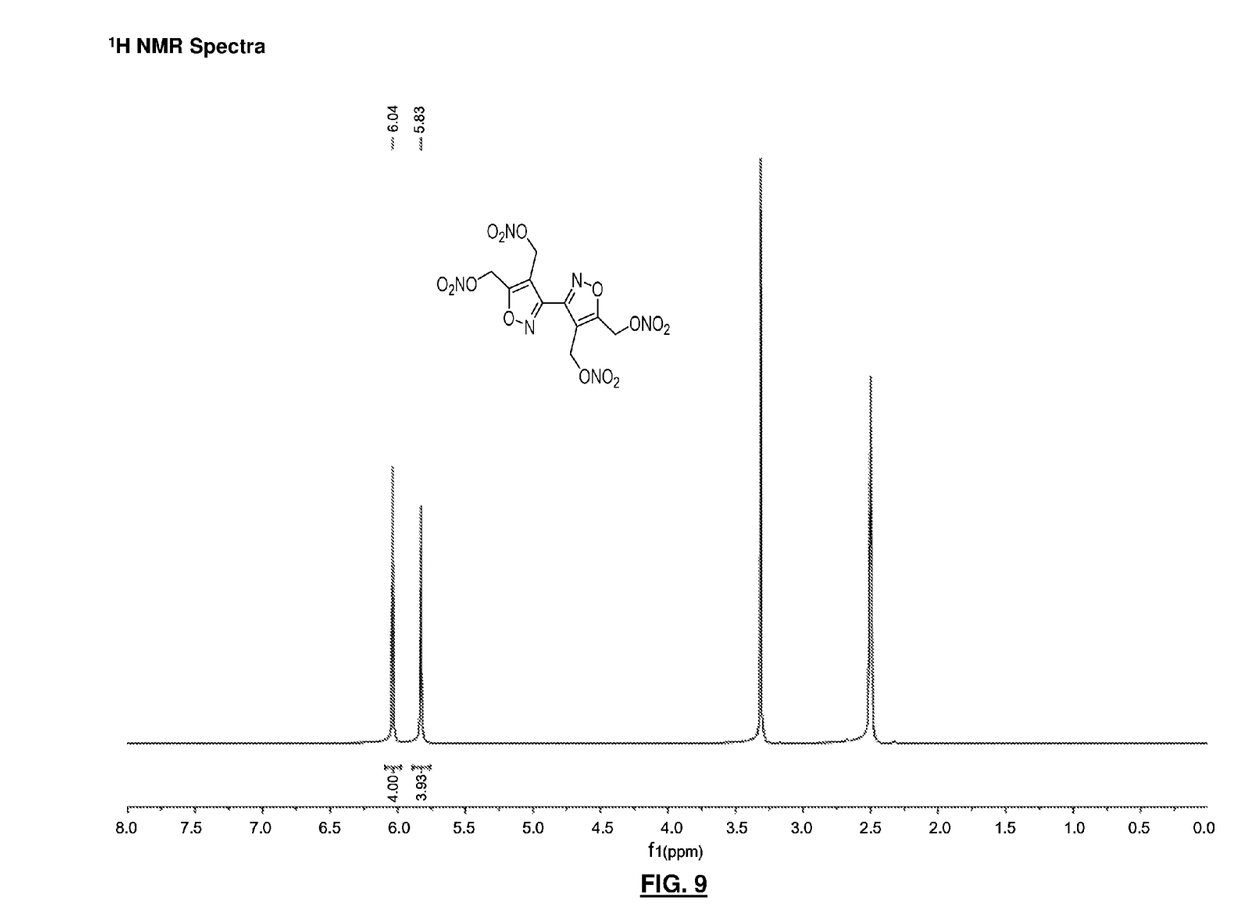
FIG. 9 is a graphical illustration of an $^1$H NMR spectra of 3,3'-bis-isoxazole-4,4',5,5'-tetrylbis(methylene) tetranitrate (BITN) according to an embodiment herein.
Figure 10:
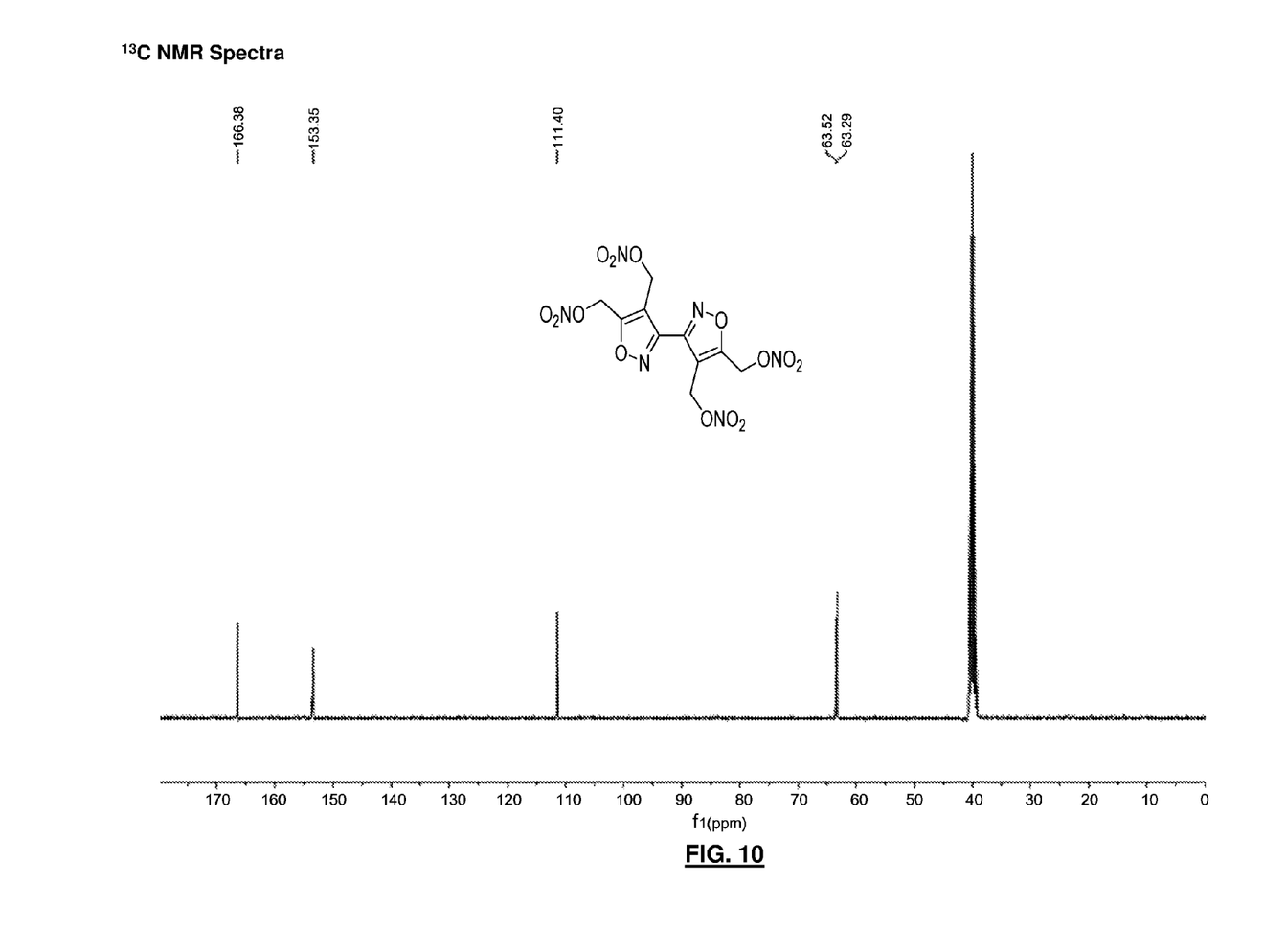
FIG. 10 is a graphical illustration of an $^{13}$C NMR spectra of 3,3'-bis-isoxazole-4,4',5,5'-tetrylbis(methylene) tetranitrate (BITN) according to an embodiment herein.

As shown in FIGS. 1 and 2, the synthesis of BITN is a multi-step process that begins with commercially available glyoxal. Glyoxal is first converted to glyoxime, and this latter molecule is then chlorinated to produce dichloroglyoxime (DCG). In a first embodiment, to a mixture of DCG and 2-butyne-1,4-diol in ethanol is added to a saturated solution of sodium bicarbonate over approximately four hours. When the reaction is performed at 0° C., no product is obtained. When the reaction is performed at 60° C., 2% of tetrol is formed. When the reaction is performed at 80° C., 12% of tetrol is formed.

In a second embodiment, to a mixture of DCG and 2-butyne-1,4-diol in n-butanol is added an aqueous solution of sodium bicarbonate over approximately four hours. When the reaction is performed at 100° C., a 34% yield of tetrol is obtained. When the reaction is performed at 120° C., 68% of tetrol is obtained.

According to the embodiments herein, creating 3,3'-bis-isoxazole-4,4',5,5'-tetryltetramethanol involves several steps and may be formulated according to the following exemplary procedure: 2-Butyne-1,4-diol (13.72 g, 0.159 mol, 5.0 eq), sodium bicarbonate (6.7 g, 0.080 mol, 2.50 eq), and 200 mL″BuOH are combined in a 1 L round bottom-3-neck-flask equipped with a stirbar and a reflux condenser. The mixture is heated to 120° C. DCG (5 g, 0.032 mol, 1.0 eq) is dissolved in 400 mL″BuOH, and added dropwise via an addition funnel over 4-6 hours. Once the addition is complete, the reaction mixture cools to room temperature, and then is concentrated in vacuo on a rotary evaporator to dryness. Ice cold water (400 mL) is added to the resulting solid material and stirred for 5 minutes. The solid is collected by Büchner filtration, washed with an additional 400 mL of cold water, and is left under suction for 3 hours. The solid is then left to dry overnight in a fume hood yielding 5.56 g (68.1%) of tetrol as a pale tan-colored powder: $T_{melt}$=183.0° C. (onset), 184.4° C. (peak) (shown in FIG. 3); IR (cm$^{-1}$): $v_{OH}$=3236.33 (m), $v_{NO}$=1622.82 (w) (shown in FIG. 4); $^{1}$H NMR (400 MHz, DMSO-d$_6$), 5.61 (broad s, 2H, —OH), 4.99 (broad s, 2H, —OH), 4.71 (s, 4H, —CH$_2$—OH), 4.59 (s, 4H, —CH$_2$—OH) (shown in FIG. 5). $^{13}$C NMR (100 MHz, DMSO-d$_6$), 170.21 (N—C—C), 152.93 (O—C—C), 115.62 (—CH), 53.27, 52.03 (—CH2-) (shown in FIG. 6).

According to the embodiments herein, creating 3,3'-bis-isoxazole-4,4',5,5'-tetrylbis(methylene) tetranitrate involves several steps and may be prepared according to the following exemplary procedure: To a 100 mL round-bottom flask equipped with a stirbar a 50 mL of 90% HNO$_3$ is added. The flask is cooled to 0° C. in an ice-water bath, and the bis-isoxazole tetrol (5.00 g, 19.5 mmol, 1.00 eq) is added portion wise over a 10 minute period. The ice-water bath is removed, and the reaction mixture is stirred for 4 hours at room temperature. The reaction mixture is then poured onto crushed ice with stirring for 15 minutes, and the solid precipitate is collected by Buchner filtration. The solid precipitate is left to dry on the Büchner funnel under suction for 3 hours, and is dried overnight in a fume hood to afford 7.24 g (85%) of 3,3'-bis-isoxazole-4,4',5,5'-tetrylbis(methylene) tetranitrate (BITN) as a white powder: $T_{melt}$=121.9° C. (onset), 125.0° C. (peak); $T_{dec}$=193.7° C. (onset), 219.1° C. (peak) (shown in FIG. 7); IR (cm$^{-1}$): $v_{NO}$=1650.53 (s) (shown in FIG. 8); $^{1}$H NMR (400 MHz, DMSO-d$_6$), 6.04 (s, 4H, —CH$_2$—ONO$_2$), 5.83 (s, 4H, —CH$_2$—ONO$_2$) (shown in FIG. 9). $^{13}$C NMR (100 MHz, DMSO-d$_6$), 166.38 (N—C—C), 153.35 (O—C—C), 111.40 (—CH), 63.52, 63.29 (—CH$_2$—) (shown in FIG. 10).

Nitration of the tetrol with 90% HNO$_3$ furnishes BITN in the optimal spherical morphology in high yield. Nitration of tetrol with 100% HNO$_3$/acetic anhydride furnishes BITN in the needle-like morphology. These processes provided by the embodiments herein do not require flash chromatography on silica gel purification throughout the synthesis of BITN. Rather, all pure products are isolated by filtration in accordance with the embodiments herein. BITN can be synthesized reproducibly at the 5 g scale. The embodiments herein provide a process of getting internal alkynes to react with hydroximoyl chlorides in the absence of a ruthenium catalyst, and instead use heating, which offers a cost-effective process. Accordingly, in addition to the BITN molecule itself, the reaction of the internal alkyne 2-butyne-1,4-diol to DCG in the presence of heat is unique in accordance with the embodiments herein.

Differential scanning calorimetry (DSC) analysis, on BITN shows that the molecule has an onset melting temperature of 121.9° C. and exothermic onset decomposition temperature of 193.7° C. The melting point of BITN is ideal to form eutectics with other energetic materials for the purposes of serving in melt-castable applications.

The sensitivity of BITN is given in Table 1. BITN has an impact, friction, and ESD sensitivity on par with PETN, and accordingly BITN is of potential use as a pyrotechnic primer ingredient.

TABLE 1

Sensitivities of 3,3'-bis-isoxazole-4,4',5,5'-tetrylbis(methylene) tetranitrate

| Compound | IS[a] [J] | FS[b] [N] | ESD[c] [J] |
|---|---|---|---|
| RDX | 6.2 | 141 | 0.0625 |
| PETN | 3.0 | 60 | 0.0625 |
| BITN | 3.0 | 60 | 0.0625 |

[a]IS = impact sensitivity, h$_{50}$ value
[b]FS = friction sensitivity
[c]ESD = electrostatic discharge The theoretical energetic properties of BITN are summarized in Table 2, which shows that BITN has power that is roughly equivalent to nitroglycerin (NG). Its high degree of power, coupled with its melting and decomposition temperatures make BITN a candidate as an ingredient for melt-castable eutectic explosives. BITN's potential as an energetic plasticizer stems from the solubility of BITN in organic solvents such as acetone, its possession of alkyl pendant primary nitrate ester chains, and its Lewis basic character owing to the N—O linkage in the isoxazoles.

TABLE 2

Properties of 3,3'-bis-isoxazole-4,4',5,5'-tetrylbis(methylene) tetranitrate

| Data category | BITN | NG | PETN |
|---|---|---|---|
| $T_m$ [° C.][a] | 121.9 | 14.0 | 141.3 |
| $T_{dec}$ [° C.][b] | 193.7 | 50.0 | 210.0 |
| $\Omega_{CO2}$ [%][c] | −36.7 | 3.50 | −10.1 |
| $\Omega_{CO}$ [%][d] | 0 | +24.7 | +15.2 |
| $\rho$ [gcm$^{-3}$][e] | 1.76 | 1.60 | 1.76 |
| $P_{cj}$ [GPa][f] | 25.6 | 25.3 | 31.5 |
| $V_{det}$ [ms$^{-1}$][g] | 7656 | 7700 | 8274 |
| $\Delta_f H°$ [kJmol$^{-1}$][h] | −393.5 | −370.0 | −538.6 |

[a]$T_m$ = onset temperature of melting
[b]$T_{dec}$ = onset temperature of decomposition
[c]$\Omega_{CO2}$ = CO$_2$ oxygen balance
[d]$\Omega_{CO}$ = CO oxygen balance
[e]$\rho$ = experimental density
[f]$P_{cj}$ = detonation pressure
[g]$V_{det}$ = detonation velocity
[h]$\Delta_f H°$ = molar enthalpy of formation The synthesized molecule, BITN is not known in the literature and industry, and hence both the molecule itself, and its synthesis, are new in accordance with the embodiments herein. Moreover, its energetic properties, impact, friction, and ESD sensitivities, and its analytical and physical properties are not known in the industry either.

The major hindrances to modern formulation, processing, and production of high-energy plasticizers are three-fold. First, many of these solvents have a preponderance to be water soluble, making them intractable for field use. Second, most hydrophobic plasticizers are so fuel-rich (triacetin and phthalates, for example) they erode performance and burn rate horribly, making them useless in large amounts. Third, molecules with strong Lewis base character chemically react with the electrophilic nitrocellulose backbone, destroying molecular weight and generating $NO_x$.

However, BITN contains a CO oxygen balance of 0%, a reasonable density, and possesses the proper characteristics to make it an excellent candidate as a neutral, energetic plasticizer and wetting agent/energetic surfactant. BITN is soluble in organic solvents such as acetone, but is insoluble in water. BITN still possesses some weak Lewis base activity (i.e., N—O isoxazole linkage) to interact with electrophilic binders and solid fillers. BITN possesses energetic, electrophilic properties to solubilize in the lacquer in typical double-base lacquers. BITN only contains primary nitrate functionalities which are known to possess good stability as compared to those with secondary nitrates. Also, the nitrates coupled with the polarized ring structure enhances the solubility in commonly used nitrate-based lacquers. Furthermore, BITN has a very high thermal stability by DSC analyses.

BITN may be utilized as an ingredient in melt-castable eutectic explosive formulations. This includes a replacement for TNT-based, RDX-based, and DNAN-based formulations. BITN may be used as an energetic plasticizer to replace diethylene glycol dinitrate (DEGDN), triethylene glycol dinitrate (TEGDN) in double-base propellant formulations. BITN may be used as an energetic plasticizer to replace the non-energetic phthalate-based, adipate-based, and triacetin-based propellant plasticizer ingredients in rocket and gun propellant applications. BITN may be used as a plasticizing ingredient that assists in making up the general formulation of double-based propellants. BITN may be used as a RDX replacement in propellant formulations to improve wetting, plasticization with NC, and to improve rho $I_{sp}$. Moreover, BITN may be used as a pyrotechnic ingredient in primer formulations.

Based on the molecular structure of BITN, its sensitivity profile to impact, friction and ESD, its energetic properties, and its analytical and physical properties, BITN may be used as a potential energetic plasticizer for use in rocket and gun propellant formulations. It is also a potential ingredient in developing high-performing melt-castable eutectic explosive formulations, and may also find use in pyrotechnic primer formulations, due to its PETN-like sensitivity.

BITN can be manipulated, depending on the nitration conditions, to exist in either the needle-like or spherical morphology. While the spherical morphology carries lower sensitivity, BITN in the needle-like morphology is potentially useful as an ingredient in pyrotechnic primer formulations. The high decomposition temperature of BITN (onset temperature of decomposition=193.7° C.) is unique, as most nitrates have decomposition temperatures around 150° C.

Figure 11:
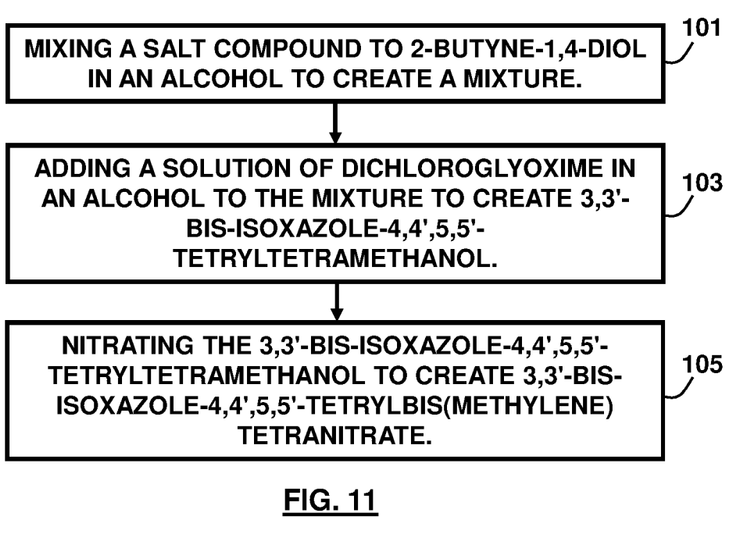
FIG. 11 is a flow diagram illustrating a method according to an embodiment herein.

FIG. 11, with reference to FIGS. 1 through 10, is a flow diagram illustrating a method according to an embodiment herein. The method comprises mixing (101) a salt compound to 2-butyne-1,4-diol in an alcohol to create a mixture; adding (103) a solution of dichloroglyoxime in an alcohol to the mixture to create 3,3'-bis-isoxazole-4,4',5,5'-tetryltetramethanol; and nitrating (105) the 3,3'-bis-isoxazole-4,4',5,5'-tetryltetramethanol to create 3,3'-bis-isoxazole-4,4',5,5'-tetrylbis(methylene) tetranitrate. The 3,3'-bis-isoxazole-4,4',5, 5'-tetrylbis(methylene) tetranitrate comprises the structural formula:

The alcohol may comprise ethanol, wherein the adding (103) may occur at 60° C., or alternatively the adding (103) may occur at 80° C. The alcohol may comprise n-butanol, wherein the adding (103) may occur at 100° C., or alternatively the adding (103) may occur at 120° C. The mixing (101) may occur at 120° C. The method may further comprise nitrating the 3,3'-bis-isoxazole-4,4',5,5'-tetryltetramethanol with nitric acid. The nitric acid may comprise at least a concentration of 90% nitric acid in water. The method may further comprise nitrating the 3,3'-biisoxazole-4,4',5,5'-tetryltetramethanol with 100% nitric acid and acetic anhydride. The adding (103) may occur over at least a four-hour period. The method may further comprise cooling the nitrated 3,3'-bis-isoxazole-4,4',5,5'-tetryltetramethanol to 0° C.; stirring the cooled nitrated 3,3'-bis-isoxazole-4,4',5,5'-tetryltetramethanol for at least four hours creating a precipitate; warming the precipitate; pouring the precipitate onto ice while stirring creating a solid material; collecting the solid material; and drying the solid material to yield the 3,3'-bis-isoxazole-4,4',5,5'-tetrylbis(methylene) tetranitrate.

As it pertains to its potential use as a melt-castable eutectic ingredient in explosives, which is a rarity for nitrate-based materials, there is a drive to replace TNT (the standard melt-castable explosive) due to environmental concerns. DNAN-based melt-castable explosives exist as an alternative to TNT. However, DNAN has lower performance than TNT, and is lower in performance than BITN. Because of the high performance of BITN, it is believed that a eutectic material could be developed that significantly exceeds DNAN. Accordingly, BITN, with its high detonation pressure and detonation velocity, could be used as an ingredient in pyrotechnic primer formulations.

As it pertains to its potential use as a propellant plasticizing ingredient, this shock sensitivity of a propellant may be reduced significantly when volatile diethyleneglycol dinitrate (DEGDN), for example, is replaced by BITN. BITN is less volatile and more thermally robust than DEGDN. The Lewis basic nature of BITN may serve as a better wetting ingredient, which may plasticize NC more effectively. The lowered vapor pressure and favorable interactions of BITN with an extensive amount of NC may improve slow cook-off and bullet/fragment impact, both of which are driven by gas phase reactions.

Replacing DEGDN with other known, less sensitive plasticizers rapidly diminishes rocket performance, as oxygen balance is pushed to fuel richer formulations. Coupled with this effect is typical loss of burning rate in operational regimes. Moreover, plasticizers such as TMETN do not plasticize/solvate nitrocellulose as well as NG at a molecular level, thus hurting mechanical and shock sensitivity properties.

BITN may be used as a plasticizing ingredient in rocket and gun propellant formulations, as a melt-castable eutectic explosive ingredient, and as a pyrotechnic primer ingredient. Since this molecule is energetic, it is possible that BITN could be used in any application where there is a need for a high-energy fuel that possesses nitroglycerin-like power. BITN may also be used in other applications including, but not limited to: (1) An ingredient in high-energy melt-castable eutectic explosive formulations. This includes a replacement for TNT-based, RDX-based, furazan-based, and DNAN-based melt-castable formulations. (2) An energetic plasticizer to replace DEGDN and TEGDN in double-base propellant formulations. (3) An energetic plasticizer to replace the non-energetic phthalate-based, adipate-based, and triacetin-based propellant plasticizer ingredients in rocket and gun propellant applications. (4) A plasticizing ingredient that assists in making up the general formulation of double-based propellants. (5) A pyrotechnic ingredient in primer formulations. (6) As a pyrotechnic primer ingredient for the manufacturing of civilian firearms. (7) As a melt-castable eutectic explosive ingredient for the replacement of DNAN-based, TNT-based, and RDX-based formulations. (8) Enhanced handling, processing and de-tooling during the use of BITN as an energetic ingredient in typical mixing, casting and curing of modern, castable minimum signature rocket propellants. (9) Pressed and/or extruded dynamite formulations where heat of explosion is often controlled only by alteration of nitroglycerin content. The use of an insensitive, yet energetic plasticizer with reduced volatility would enhance the manufacture, transportation, and storage of new types of dynamites. Likewise, higher thermal stability with lower vapor pressure and slower aging may offer advantages in high thermal performance areas such as those in underground mining and deep petroleum fracking.

While it is known that the use of non-energetic plasticizers of nitrocellulose such as triacetin, do decrease sensitivity and enhance processing and safety. However, this comes at the cost of performance, both in specific impulse and typically with a reduction of the heat of explosion. Thus, a lowering of burning rate in typical motor operational pressure regimes is typically achieved. BITN provides enhanced energy and enhanced processing safety and handling to the overall propellant making for a more competitive, less sensitive version of said propellant since it may plasticize nitrocellulose more effectively. Similarly, BITN may not take large mass quantities with specific formulations to make major improvements to processing safety, handling, tooling and machining of such propellants. BITN may provide plasticization of higher nitrogen nitrocellulose stocks (typically >12.6% N content), allowing for the use of higher nitrogen content nitrocellulose with higher resultant mechanical properties. Typical energetic plasticizers used in minimum signature propellants either as extruded or castable, notably nitroglycerin (NG) and 1, 2, 4-butane-triol-trinitrate (BTTN) suffer from high mechanically sensitivity (impact, friction) and/or thermal stability issues since they contain secondary nitrate ester functionalities. Since BITN contains only primary nitrate functionalities, it may offer reduced cost in aging, surveillance, and demilitarization costs with longer propellant shelf lives with reduced aging issues often typical of double base propellant based on energetic nitrate ester plasticizers which contain secondary nitrate ester functionalities. Finally, higher thermally stable propellants using BITN as an energetic plasticizer can exhibit lower vapor pressure and slower aging. This may offer opportunities during typical tactical platforms exposed to large thermal extremes or extended periods of thermal stress with lowered migration rates within and out/into propellants to the external environment and/or liner.

Another element that hinders most commonly fielded double-base minimum signature castable propellants is poor responses to bullet/fragment insults, slow cook off scenarios, and shape charge jet threats. Much of this is due to the high volatility and reactivity of the entrained nitrate ester plasticizer notably nitroglycerine when subjected to such scenarios. Accordingly, BITN offers significant improvements in this regard, with its higher molecular interactions within the plasticizer matrix of the formulations, resulting in more homogenous, less sensitive propellants.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:
1. A method comprising:
    mixing a salt compound to 2-butyne-1,4-diol in an alcohol to create a mixture;
    adding a solution of dichloroglyoxime in an alcohol to said mixture to create 3,3'-bis-isoxazole-4,4',5,5'-tetryltetramethanol; and
    nitrating said 3,3'-bis-isoxazole-4,4',5,5'-tetryltetramethanol to create 3,3'-bis-isoxazole-4,4',5,5'-tetrylbis(methylene) tetranitrate.
2. The method of claim 1, wherein said alcohol comprises ethanol.
3. The method of claim 2, wherein the adding occurs at 60° C.
4. The method of claim 2, wherein the adding occurs at 80° C.
5. The method of claim 1, wherein said alcohol comprises n-butanol.
6. The method of claim 5, wherein the adding occurs at 100° C.
7. The method of claim 5, wherein the adding occurs at 120° C.
8. The method of claim 1, wherein the mixing occurs at 120° C.
9. The method of claim 1, further comprising nitrating said 3,3'-bis-isoxazole-4,4',5,5'-tetryltetramethanol with nitric acid.
10. The method of claim 9, wherein said nitric acid comprises at least a concentration of 90% nitric acid in water.
11. The method of claim 1, further comprising nitrating said 3,3'-biisoxazole-4,4',5,5'-tetryltetramethanol with 100% nitric acid and acetic anhydride.
12. The method of claim 1, wherein the adding occurs over at least a four-hour period.
13. The method of claim 1, further comprising:
    cooling the nitrated 3,3'-bis-isoxazole-4,4',5,5'-tetryltetramethanol to 0° C.;

stirring the cooled nitrated 3,3'-bis-isoxazole-4,4',5,5'-tetryltetramethanol for at least four hours creating a precipitate;
warming said precipitate;
pouring said precipitate onto ice while stirring creating a solid material;
collecting said solid material; and
drying said solid material to yield said 3,3'-bis-isoxazole-4,4',5,5'-tetrylbis(methylene) tetranitrate.

14. A compound having the structural formula:

* * * * *